(12) United States Patent
Onwumere et al.

(10) Patent No.: US 6,436,713 B1
(45) Date of Patent: Aug. 20, 2002

(54) METHODS AND DEVICES FOR MEASURING TOTAL POLAR COMPOUNDS IN DEGRADING OILS

(75) Inventors: Fidelis C. Onwumere, Mansfield, TX (US); Robert A. Pranis; Jack G. Truong, both of St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/446,375

(22) PCT Filed: Jul. 28, 1997

(86) PCT No.: PCT/US97/13168

§ 371 (c)(1),
(2), (4) Date: Dec. 20, 1999

(87) PCT Pub. No.: WO99/05519

PCT Pub. Date: Feb. 4, 1999

(51) Int. Cl.[7] .............................................. G01N 31/22
(52) U.S. Cl. ......................... 436/56; 422/68.1; 422/99; 422/101
(58) Field of Search ...................... 422/68.1, 56, 99, 422/101

(56) References Cited

U.S. PATENT DOCUMENTS

| | | | |
|---|---|---|---|
| 2,770,530 A | 11/1956 | Bergstrom | 23/230 |
| 2,953,439 A | 9/1960 | Elliott et al. | 23/230 |
| 3,030,190 A | 4/1962 | Seeman et al. | 23/230 |
| 3,615,226 A | 10/1971 | Apter | 23/230 R |
| 4,349,353 A | 9/1982 | Blumenthal et al. | 23/230 R |
| 4,582,684 A | * 4/1986 | Vogel et al. | 422/57 |
| 4,623,638 A | 11/1986 | Hayatsu et al. | 502/401 |
| 4,654,309 A | 3/1987 | Mlinar et al. | 436/61 |
| 4,988,627 A | * 1/1991 | Smith-Lewis | 436/165 |
| 5,082,626 A | * 1/1992 | Grage, Jr. | 422/56 |
| 5,356,667 A | 10/1994 | Hench et al. | 427/384 |
| 6,140,134 A | * 10/2000 | Rittenburg | 436/154 |

OTHER PUBLICATIONS

"Determination of Polar Compounds Content in Animal and Vegetable Fats and Oils", International Organization for Standardization, IS 8420, pp. 1–5, 1990.

"Practice of Thin Layer Chromatograpy", Joseph C. Touchstone, Department of Obstetrics and Gynecology, University of Pennsylvania, p. 25, 1992.

"A Comparative Study of Analytical Methods for Quality Evaluation of Frying Fat", Croon et al., pp. 87–91, 1986.

"Regulation of Frying Fats and Oils", *Food Technology*, pp. 90–93, Feb., 1991.

Operating Manual—Food Oil Sensor, Northern Instruments Corp. pp. 1–11.

* cited by examiner

Primary Examiner—Jill Warden
Assistant Examiner—Monique T. Cole
(74) Attorney, Agent, or Firm—Michaele A. Hakamaki; Peter L. Olson; Kevin H. Rhodes

(57) ABSTRACT

The invention relates to methods for determining whether or not to discard a sample of oil based on the presence of polar compounds in oil and devices to be used to determine the presence of polar compounds in oil. In a preferred embodiment, a test strip comprising an adsorbent affixed to a backing is spotted with a polar indicator. A sample of oil is positioned on a heat conducting device supporting the test strip and the oil is allowed to migrate over the adsorbent material, thereby displacing the polar indicator in an amount related to the amount of polar compounds in the oil. This displacement is correlated to the amount of polar compounds in the sample.

20 Claims, 7 Drawing Sheets

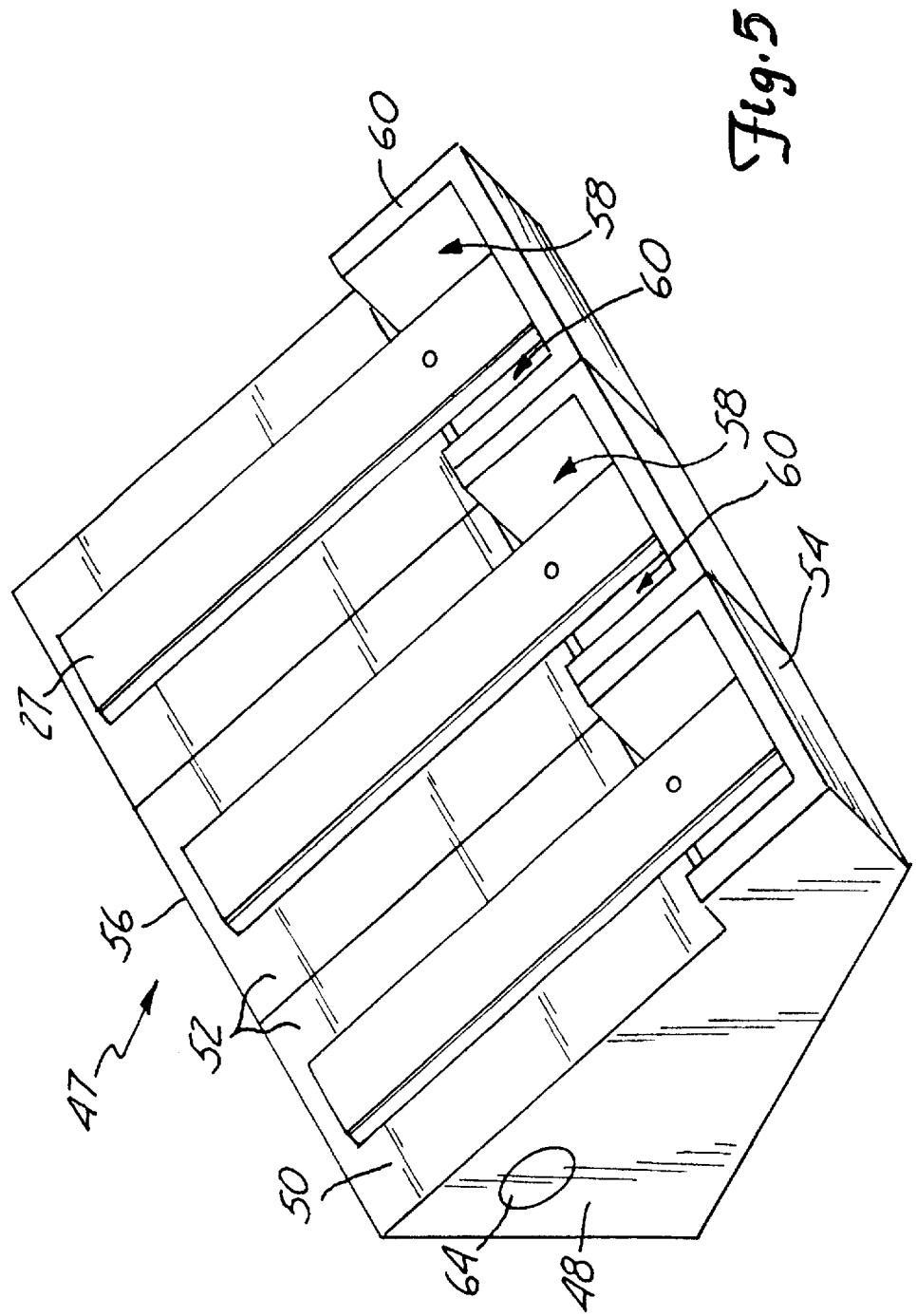

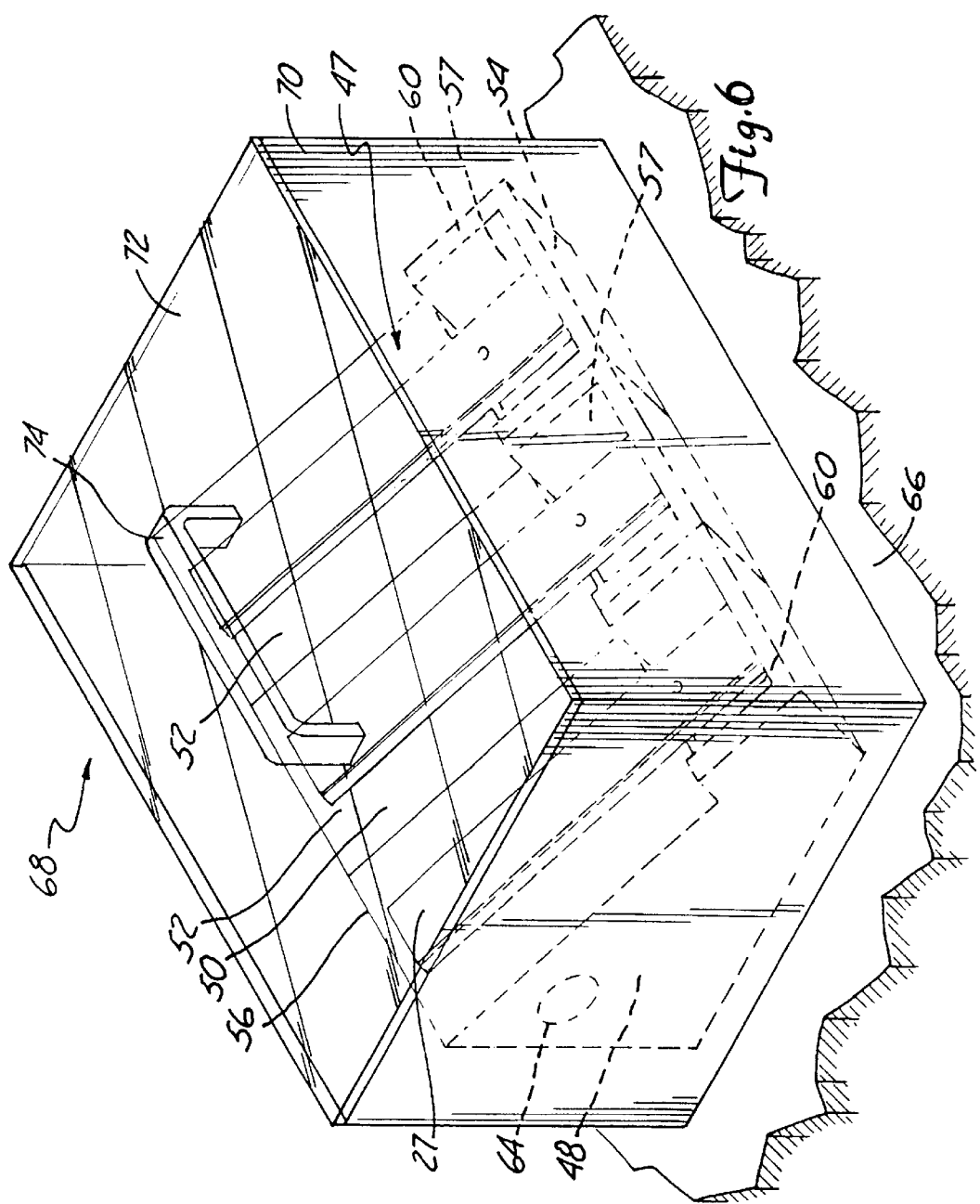

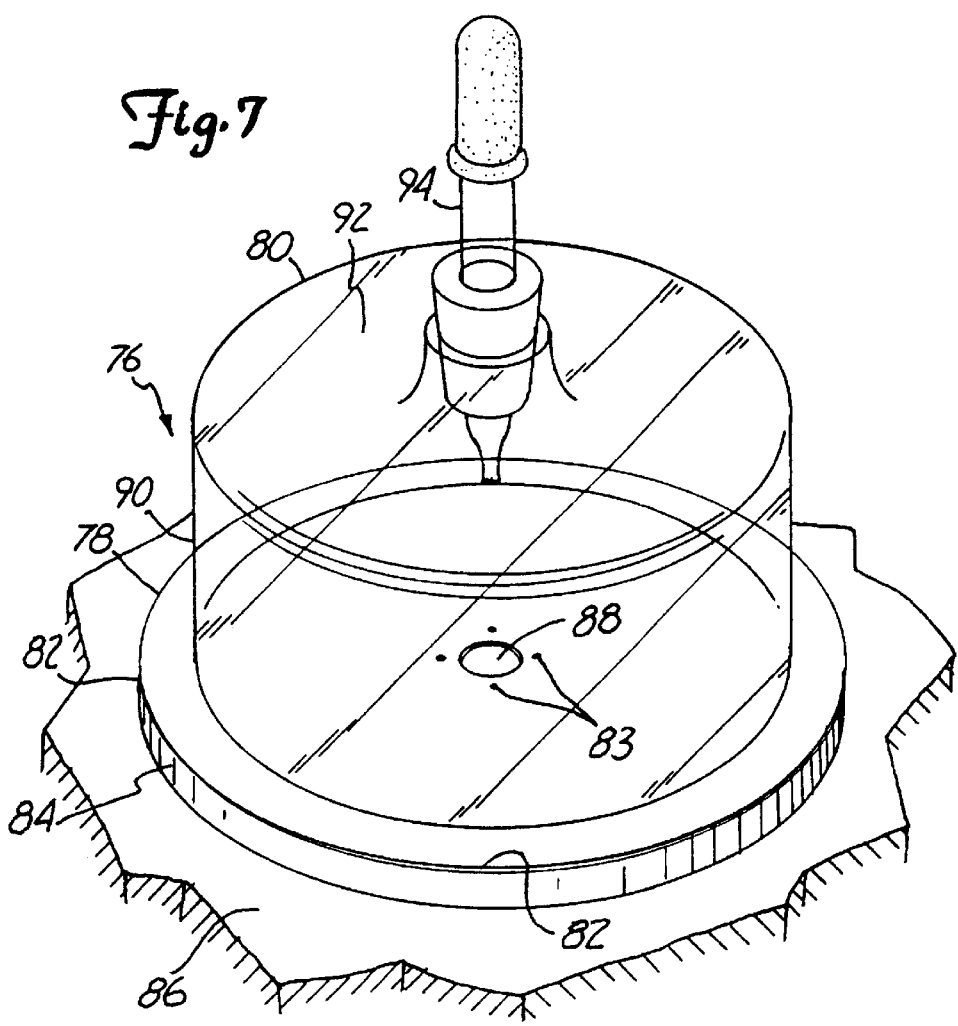
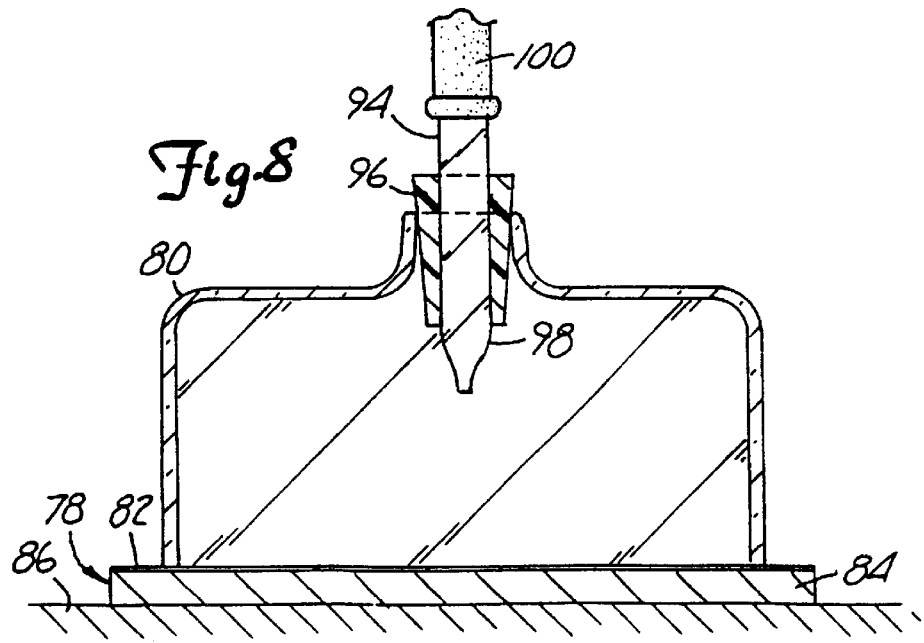

METHODS AND DEVICES FOR MEASURING TOTAL POLAR COMPOUNDS IN DEGRADING OILS

FIELD OF THE INVENTION

The present invention relates to methods and devices for identifying the presence and quantifying the amount of polar compounds in oils resulting from the breakdown of the oils from use or storage.

BACKGROUND OF THE INVENTION

When oils (used herein to refer to oils, fats, shortenings and mixtures thereof) are heated in the presence of oxygen and water, thermolytic and oxidative reactions take place, resulting in the degradation of the oils. Most edible oils are triglycerides formed from the reaction of fatty acids and glycerol. Oils are generally considered non-polar in their pure form. However, some oils contain from about 0.5% to about 2% free fatty acids. The presence of these fatty acids may impart some polarity to the fresh oils. However, as these oils are heated at high temperatures (for example, under conditions of deep-frying or under high shear and pressure conditions as can be found for some synthetic oils), the oils can oxidize, polymerize, and/or hydrolyze. Oxidation can generate new functional groups in the hydrocarbon chain of the triglyceride and hydrolysis can generate free fatty acids, monoglycerides and diglycerides. These processes can increase the polarity of the oils.

A number of methods exist in the literature to detect degraded products in oils. Most of the methods are specific to a particular degradation pathway or assay for a particular chemical change. For instance, the measurement of free fatty acids in oil can be used to estimate the level of degradation of oils by the hydrolysis pathway. This method does not quantify the total polar compounds in the oils. Other methods to assess the degradation of oils include, but are not limited to, the determination of hydroxyl number, iodine value, carbonyl value, decreases in unsaturation, smoke point and viscosity changes. There are commercial devices to detect one or more changes in oil that occur with use and each of these methods has its own drawbacks. For example, the FOODOIL-SENSOR (Northern States Instrument, Circle Pines, Minn.) monitors the change in the dielectric constant of frying oils but this instrument must be calibrated to fresh oil daily. Because different oils have different dielectric constants, separate information must be provided for each type of oil to determine whether or not the change in the dielectric constant of a particular oil indicates the oil should be discarded. These types of instruments may not give consistent results over time because the test is also sensitive to environmental factors, such as air drifting, or sensitive to the presence of food particles in the oil itself. The instruments do not operate well in a draft, such as occur in locations near ventilating systems that circulate air. Many deep-fat fryers are positioned under or close to strong air uptake currents making the test ill-suited for use in some restaurants. Libra Labs (Metuchen, N.J.) and U.S. Pat No. 4,349,353 to Blumenthal disclose tests to detect the presence of alkaline compounds that accumulate in used frying oils. U.S. Pat. No. 4,623,638 to Hayatsu et al. discloses a silica gel that absorbs and desorbs polycyclic organic substances in a solution to detect and remove mutagenic substances from the environment and foodstuffs.

Colorimetric tests based on the pH of the oil are available. For example, the OXIFIT test (E. Merck, Darmstadt, Germany) is a colorimetric test kit that contains redox indicators that react with the total amount of oxidized compounds in the oil. The 3M Shortening Monitor (Minnesota Mining and Manufacturing, St. Paul, Minn.) is a paper strip containing base as an indicator that changes color when the base reacts with fatty acids in the oil. A FRITEST (E. Merck) is available and is a colorimetric test kit that is sensitive to carbonyl compounds. Robern and Gray teach a spot test (*Can. Inst. Food Sci. Technol. J.* 14:150, 1981) that is a colorimetric test that monitors the free fatty acid content of the oil based on the pH of the oil. The diagnostic colors of the pH indicator are blue, green and yellow. Alkaline contaminant materials can also be detected in oils. Other colorimetric tests include those of U.S. Pat. Nos. 2,770,530; 3,030,190; 3,615,226; and 2,953,439.

Colorimetric tests can be problematic because the color indicators should be readily visualized from the background colors of the test. Colors such as yellow, light reds or light greens can be difficult to read because the degraded oils can also be colored.

One of the factors determining the cooking quality of used frying oils is the amount of breakdown products in the oil. The amount of polar compounds in oil is important because, for example, the presence of increased amounts of polar compounds detrimentally affect taste and oil viscosity. For example, increased amounts of polar compounds tend to produce a less viscous oil and this characteristic impacts the permeability of the oil into food, for example, in a frying apparatus. In general, reduced penetration of oils into foods is preferred for appearance, taste and health reasons.

A number of European countries have specific regulations for frying oils. Some of the European countries have regulations to restrict the amount of polar materials in oils. For example, Austria, Belgium, France, Germany, Hungary, Italy, Spain and Switzerland require, depending on the country, no more than between 2%1 to 27% polar compounds in oils used with food. The German government has determined that the presence of 27% polar compounds corresponds to 0.7% of oxidized fatty acids insoluble in petroleum ether (Firestone, D. et al. "Regulation of Frying Fats and Oils" in *Food Technology* February 1991, pp 90–93), and that levels above this amount are not acceptable. It is likely that agencies of other governments will also institute regulations and quality assurance guidelines requiring the regular replacement of oil.

Many users of oxidative-sensitive and hydrolysis-sensitive oils employ routine periodic replacement programs to ensure that the oils maintain a useful taste and consistency. For a restaurant or a fast-food chain, it is difficult to evaluate the quality of the used cooking oil while on the restaurant premises other than by merely looking at its color, smelling the oil and/or observing the frying properties. Some restaurants with heavy fry demands and those with higher quality standards may discard and replace their oils after a relatively short time, irrespective of taste or consistency. A routine discard policy can be costly. A method to assess oil that is rapid and easy to use could save restaurants the time and money required to routinely and blindly replace their oil.

Thin layer chromatography (TLC) was originally developed as a method for separating lipids. TLC involves the use of a thin layer of adsorbent (e.g., silica gel) coated over a backing or solid surface such as glass, or the like. A sample to be analyzed is placed on the adsorbent and an edge of the thin layer is exposed to a solvent that travels up the thin layer, separating the compounds within the sample based on their relative affinities for the solvent and the adsorbent. The compounds can be identified by comparison of the separated sample with known standards.

In general, the technique has excellent resolving power and can be adapted to measure a variety of chemical constituents in a test sample. Where TLC is used to determine the amount of polar compounds in oil, a test sample is spotted onto a TLC plate and the plate is subjected to a solvent, such as petroleum ether, diethyl ether or glacial acetic acid. The solvent wicks up the adsorbent, toward the test sample. The test sample separates based on the relative affinities of the solvent and the test sample for the reactive groups on the adsorbent coating. The less polar compounds travel along the TLC plate faster than highly polar compounds. In this way TLC is used to detect the polar constituents in a test sample. TLC is a relatively sophisticated technique that is generally employed by scientists in a laboratory setting.

The American Oil Chemists' Society have standard methods for evaluating the quality of freshly refined cooking oil, including the amount of polar compounds in the oil. This method is published by the International Organization for Standardization and is provided as a publication ISO 8420:1990(E) entitled "Determination of Polar Compounds Content in Animal and Vegetable Fats and Oils" herein after referred to as "ISO 8420"). Other methods for quantifying the amount of polar compounds in oil include High Pressure Liquid Chromatography (HPLC), Liquid Chromatography (LC), Gas Chromatography (GC), and the like. ISO 8420 and other current procedures that quantify the amount of polar compounds in oil are. complex and impractical for the cooking staff in an eating establishment.

The tests that are currently commercially available can have a number of problems. Many of the methods currently available for testing oil quality require expensive equipment that must be calibrated on a regular basis. These tests measure the polar compounds in oil indirectly. For example, pH changes are an indirect measure of the amount of polar compounds in an oil. A number of these tests require laboratory skill and periods of time greater than 2–3 hours.

Consequently, a long felt need exists for a quick reliably and easily performed test method to determine the amount of polar compounds in oil. A further need exists for a device to facilitate the performance of such a method.

SUMMARY OF THE INVENTION

This invention provides a rapid method for determining polar compounds in a sample of oil. The method is not prone to environmental factors such as air drifting or the presence of particles in the oil. The results of the test are produced rapidly and consistently. A device is provided that is easy to operate and can be used in any environment where heated oils are used.

The invention relates to a method for determining the presence of polar compounds in oil comprising the steps of: providing a test surface comprising an adsorbent on a backing and a polar indicator positioned at a first position on the adsorbent; contacting a portion of the test surface with a sample of oil comprising polar compounds; and allowing the front of the oil to migrate past the first position and thereby mobilize the polar indicator. The method of this invention can also additionally comprising the steps of: taking the ratio of the distance that the polar indicator has moved on the adsorbent to the distance the oil front has moved relative to a fixed point on the adsorbent to generate an Rf value for the oil; and using the Rf value to determine the presence of polar compounds in the oil. The fixed point is preferably a portion of the test surface.

In this method, the adsorbent is preferably selected from the group consisting of silica, aluminum oxide, and cellulose and the backing is preferably selected from the group consisting of glass, paper, aluminum and heat-resistant plastic. The oil is preferably selected from the group consisting of lard, corn oil, peanut oil, canola oil, olive oil, palm oil, palm kernel oil, coconut oil, red palm oil, and mixtures thereof In one embodiment, the polar indicator is a polar colored dye and preferably the polar dye is ESTOFIL-BLUE S-RLS (Sandoz Chemicals Export, available from Clariant Corp. Charlotte, N.C.) and preferably the polar indicator is a dye that has less affinity for the adsorbent than the polar compounds in the oil and more affinity for the adsorbent than unused oil.

The invention also relates to a device for determining polar compounds in oil comprising: a base; at least one side adjacent to the base; at least one sample reservoir; and at least one heat-conducting support surface adapted to support at least one test surface wherein the test surface is in fluid communication with at least one sample reservoir when oil is in the sample reservoir, the support surface is angled relative to a plane containing the base of the device to provide an elevated support surface relative to the sample reservoir and wherein the sample reservoir is adapted to receive an oil sample and a portion of the test surface. The device can additionally comprising a cover and the cover is preferably adapted to fit over the device. In one embodiment, the cover comprises a transparent portion and the cover can also comprise a handle.

The device can be adapted to test a single oil sample or a plurality of oil samples. Preferably the angle of the support surface relative to the base is about 10° to about 80° and in one embodiment, the angle of the support surface relative to the base is about 20° to about 70°. In one embodiment, the device comprises a heat-conducting material and the device can comprise a solid block of a heat conducting material. In one embodiment, the device comprises a test surface, the test surface comprising an adsorbent on a backing. Preferably the adsorbent further comprises a polar indicator.

The device can also comprise a temperature indicator and in one embodiment the device includes a heat source housed in the device.

The invention also relates to a system for determining polar compounds in oil comprising: a heat conducting device comprising a base, at least one sample reservoir adapted to contain a sample of oil comprising polar compounds, and at least one support surface adapted to support at least one test surface; wherein the support surface is angled relative to a plane containing the base of the device and wherein the sample reservoir is in fluid communication with the test surface when oil is in the sample reservoir; and at least one test surface comprising an adsorbent positioned on a backing wherein the adsorbent comprises a polar indicator. The system can also comprises a cover adapted to cover the heat conducting device. In one embodiment the cover comprises a transparent portion and the cover can also include a handle. The device of the system can be adapted to include a plurality of sample reservoirs.

In one embodiment of the system the device has a support face with an angle relative to a plane containing the base of the device of about 10° to about 80°. Preferably, the angle of the support surface relative to the base of the device is about 20° to about 70°. The device can comprise a heat-conducting material and in one embodiment, the device comprises a solid block of a heat-conducting material. The device can further comprises a temperature indicator and the temperature indicator can be included in the cover. In one embodiment the heat conducting device is prepared from a material selected from the group consisting of aluminum, copper, stainless, steel, iron, zinc and tin.

The adsorbent used in the test surface is preferably selected from the group consisting of silica, aluminum oxide, and cellulose and the backing is preferably selected from the group consisting of glass, paper, aluminum and heat-resistant plastic. The oil is preferably selected from the group consisting of lard, corn oil, peanut oil, canola oil, olive oil, palm oil, palm kernel oil, coconut oil, red palm oil, and combinations thereof In one embodiment, the device further comprises a heat source housed in the device. The polar indicator can be a polar colored dye and preferably the dye has less affinity for the adsorbent than the polar compounds in the oil and more affinity for the adsorbent than unused oil. In one embodiment, the dye is ESTOFIL BLUE S-RLS.

The invention also relates to a method for determining whether to discard oil containing polar compounds comprising the steps of: introducing a sample of oil into a sample reservoir in fluid communication with an adsorbent comprising a polar indicator wherein the adsorbent is positioned on a backing; allowing the oil sample to migrate onto the adsorbent and mobilize the polar indicator; wherein the ratio of the distance the polar indicator migrates relative to the distance the oil front migrates is proportional to the amount of polar compounds in the oil. In one embodiment, the method further comprises heating the backing. The method can also include the step of covering the adsorbent with a cover. In this method the adsorbent is preferably selected from the group consisting of silica, aluminum oxide and cellulose and the backing is preferably selected from the group consisting of glass, paper, aluminum, fiberglass and heat-resistant plastic. In one embodiment the oil is selected from the group consisting of lard, corn oil, peanut oil, canola oil, olive oil, palm oil, palm kernel oil, coconut oil, red palm oil, and mixtures thereof. In one embodiment the polar indicator is a polar colored dye and preferably the polar indicator is a dye that has less affinity for the adsorbent than the polar compounds in the oil and more affinity for the adsorbent than unused oil. In one embodiment the polar dye is ESTOFIL BLUE S-RLS.

In another aspect of this invention, the invention relates to a device for determining polar compounds in oil comprising: an adsorbent covering a backing having a sample reservoir positioned on the backing and a sample of polar indicator positioned on the adsorbent; and a cover adapted to fit over the sample reservoir and sample of polar indicator. Preferably, the adsorbent is selected from the group consisting of silica, alumina oxide, and cellulose. Preferably, the backing is selected from the group consisting of glass, paper, aluminum, fiberglass and heat-resistant plastic. The polar indicator is a polar colored dye and preferably the polar indicator is a dye that has less affinity for the adsorbent than the affinity of the polar compounds in the oil for the adsorbent and wherein the polar indicator has more affinity for the adsorbent than unused oil.

The invention further relates to a device for determining polar compounds in oil comprising: a base; at least one test surface comprising an adsorbent, with a polar indicator positioned thereon, and a backing wherein the test surface is angled relative to the plane containing the base; and at least one sample reservoir positioned adjacent to the test surface to establish fluid communication therewith when oil is present in the sample reservoir. In one embodiment the device additionally comprises a cover. Preferably, the angle of the test surface relative to the base is about 10° to about 80°.

BRIEF DESCRIPTION OF THE FIGURES

FIG. 5 is a perspective view of a second device according to this invention.

FIG. 6 is a perspective view of the device of FIG. 5 covered with a covering according to this invention.

FIG. 7 is a perspective view of a third device according to this invention.

FIG. 8 is a side-elevational view in cross-section of the device of FIG. 7.

DETAILED DESCRIPTION OF THE PREFERRED EMBODIMENTS

Figure 1:
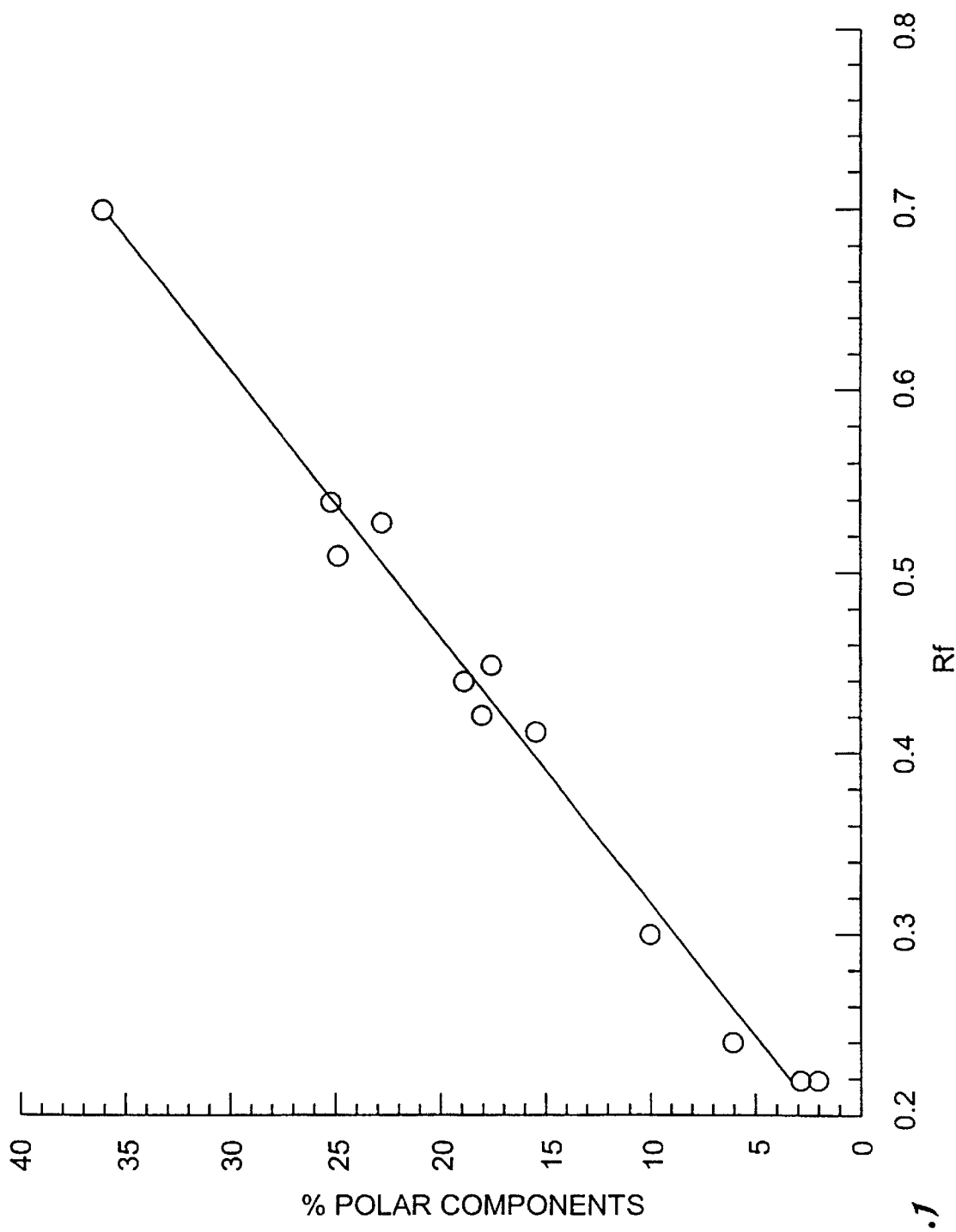
FIG. 1 is a graph correlating the percentage of polar compounds as measured by the test method ISO 8420 with the Rf determined according to the present invention. The Rf refers to the ratio of the distance the polar indicator traveled from a fixed point on the adsorbent or backing to the distance the oil traveled (i.e., the oil front) from the same fixed point on the adsorbent or backing.

The term "polar compounds in oil" as used herein, refers to the constituents of oils, fats, shortenings and mixtures thereof that can be determined by column chromatography under the conditions specified in ISO 8420:1990(E) (supra). Polar compounds include polar substances which occur in unused fats, such as monoglycerides, diglycerides, alcohols and free fatty acids, as well as polar transformation products formed during heating at temperatures and under conditions normally occurring during the frying of food in oil.

The term "oil" as used herein includes oils, fats, and shortenings. Preferably, the oils are liquids under the test conditions of this invention. The oils that can be tested in this method for the presence of polar groups include both naturally occurring as well as manufactured and synthetic oils. Synthetic oils include triglycerides or esters of polyfunctional alcohols and fatty acids. Synthetic oils can also be made from polyfunctional carboxylic acids with fatty alcohols. Most natural oils (vegetable and animal sources) are triglycerides from polyfunctional alcohols (e.g., glycerol) and fatty acids.

In one aspect of this invention, the invention relates to a method for determining the presence of polar compounds in oil based on the ability of the oil to displace a polar indicator on an adsorbent. The adsorbent is selected based on its ability to bind with a polar indicator and for the polar indicator to be displaced by the polar compounds in the oil for binding sites on the adsorbent. In this embodiment, a polar indicator is added to an adsorbent positioned on a solid surface. The oil is introduced onto the adsorbent and is allowed to migrate over the adsorbent for a time sufficient for the oil to migrate past the point where the polar indicator was added to the adsorbent and preferably prior to the time that the advancing front of the oil has migrated the entire length of the adsorbent. The polar indicator is preferably a polar dye that has less affinity for the adsorbent as compared to the polar compounds in the oil and more affinity for the adsorbent as compared to the oil in its freshest form (i.e., the oil in a quality that the user is likely to purchase, prior to a time when the oil is subjected to extreme heat). The amount of oil tested in the sample is at least enough to saturate the adsorbent. That is, there is more oil present in the test sample than the volume of oil required to saturate the adsorbent on the solid surface.

Two measurements can be taken on the adsorbent after the polar indicator has been mobilized by the oil. One measurement is the distance that the polar indicator front travels relative to a fixed point on the backing or adsorbent, such as the place where the polar indicator was initially added to the adsorbent or backing or the point where the oil was introduced onto the adsorbent or backing such as the base of the backing. Another measurement is the distance that the oil front travels relative to the same fixed point on the adsorbent or backing. A ratio of the distance the polar indicator traveled from a fixed point on the adsorbent or backing to the distance the oil traveled (i.e., the oil front) from the same fixed point on the adsorbent or backing is used to create a value, here referred to as "Rf." The Rf reading is a value that, when compared to a reference Rf value, is used to determine whether or not a particular oil sample should be discarded. The term "reference Rf value" is used herein to refer to a predetermined value relating to the degradative state of an oil. This value can be set, based on government regulations, or the value can be set as a quality assurance value for a particular restaurant or restaurant chain.

The reference Rf value determining whether or not a particular oil sample should be discarded can vary for a particular oil application, from user to user, and/or depending on government imposed regulations, from country to country. For some European countries, a percentage of polar compounds in animal and vegetable oils of greater than 25% is not permitted under specific laws or regulations related to consumer safety. This value can be correlated to an Rf range for a given device, to a select Rf value, and to a given adsorbent according to this invention. For other countries, it is known that the presence of polar compounds in oils can affect taste and/or color. Therefore, while regulatory agencies may set some threshold level, some restaurants-may elect to use a substantially lower Rf threshold than may be required by law or regulation. The reference Rf value corresponding to a percentage of total polar compounds in the oil can be set by government intervention, by user preference or by both.

A variety of synthetic and naturally occurring oils can be tested using the methods of this invention. For example oils used in cooking can be tested using these methods. These oils include, but are not limited to, proprietary and non-proprietary mixtures of oils used for frying foods, as well as lard, corn oil, peanut oil, canola, olive, palm, palm kernel oil, coconut, red palm oil, and the like. Preferably the oils tested in this invention have an Rf of about 0.2 to about 0.9 in their unused form, generally their freshest form. That is, the oils should include a sufficient amount of polar compounds to mobilize the polar indicator from its point of application to a measurable distance from the point of application to ensure that the polar indicators selected for use in the assay of the invention will be mobilized over a range of oil degradation.

Where the oil is a solid at room temperature or is too viscous to move across a substrate in a reasonable amount of time at room temperature (preferably, less than about one hour, more preferably, less than about 30 minutes, and still more preferably, less than about 25 minutes), the oil can be heated. Preferably, the oil is not heated higher than the temperature recommended for frying. Typically this is no higher than about 1 80° C., and generally it is about 160° C. to about 170° C.

The adsorbent used in this invention is generally of the type used in thin layer chromatographic separations. Acceptable adsorbents include a variety of adsorbents that preferably do not react with the oil being tested. That is, the oil migrates over the adsorbent surface in a uniform manner displacing the polar indicator and producing an Rf value that is lower for unused, generally, fresh oil and higher for used oils. Exemplary adsorbents include, but are not limited to, silica, aluminum oxide, cellulose, and sugars. The adsorbent is preferably positioned on, coated on, or covers a solid surface or backing. The terms "solid surface" and "backing" are used interchangeably throughout this disclosure. The adsorbent is preferably dry on the solid surface. Preferably the solid surface is planar and preferred solid surfaces include, but are not limited to, glass, paper, aluminum or other suitable metal, fiberglass, or a heat-resistant plastic. If a plastic solid surface or other potentially heat sensitive surface is to be used, the plastic solid surface should be prepared from a material that can withstand the test method temperature without deformation or appreciable softening. The adsorbent on a solid surface of this invention can be prepared using methods known in the art, or it can be purchased commercially. Other suitable adsorbents on a solid surface or backing include reversed phase silica, and the like. A preferred adsorbent on a backing is a silica coated glass plate (such as those commercially available from Analtech Co., Newark, Del.). These and other commercially available adsorbent covered or coated backings, such as glass plates, can be cut into a variety of sizes and shapes such as circles or strips or used in their commercially available form. For example, a variety of thin layer chromatography plates can be used. The terms "test strip" or "test surface" are used interchangeably herein refer to a solid surface coated with an adsorbent. Preferably the test strip includes a polar indicator spot created by the placement of a sample of polar indicator on the adsorbent.

In a preferred embodiment of this invention the polar indicator is a polar dye, such as dyes having hydroxy groups, carboxylic acid groups, ketone groups, aldehyde groups, and the like. The polar indicators are preferably polar dyes and the polar indicators preferably have less affinity to the adsorbent as compared to the polar compounds in the oil and more affinity for the adsorbent as compared to the oil in its unused, generally freshest form. The polar indicators selected for use in this invention are heat-resistant at the temperatures used to practice the invention.

There are a variety of dyes that could be tested for use in this invention and these dyes can be used in their known form and/or in a chemically modified such as, chemical modifications including, but not limited to, sulfonation, amidation, oxidation and/or hydrolysis to increase the polarity of a particular dye. Examples of dyes that could be useful in their present form or in a chemically modified form include dyes available under the following tradenames or designators including, but not limited to, DISPERSE BLUE dyes such as DISPERSE BLUE dye numbers 23, 28, 34, 60, 79, 79:1 and 148 corresponding to CI numbers (color index) 61545, 62065, 61510, 61104, 11345, 11344, 11124 respectively; disperse red 2, other DISPERSE RED dyes such as dye numbers 3, 19 and 92 with CI numbers of 60507, 11130, and 60752, respectively; DISPERSE VIOLET dyes including DISPERSE VIOLET dye numbers 4, 6, 17, 26 and 33 corresponding to CI numbers 61105, 61140, 60712, 62015 and 11218, respectively; REACTIVE BLUE 6 (CI number 61549); SOLVENT BLUE dyes including, but not limited to SOLVENT BLUE dye numbers 14 (CI number 61555), 35 (CI number. 61554), 59 (CI number 61552), 45 (ESTOFIL BLUE S-RLS, Sandoz Chemicals Export, available from Clariant Corp., Charlotte, N.C.), and 104 (ESTOFIL BLUE S-RBL, Clariant Corp., Charlotte, N.C.); SOLVENT BLUE 97; SOLVENT GREEN 3 (CI number 61565), SOLVENT YELLOW 43, and SOLVENT RED dyes such as SOLVENT RED numbers 44, 45 and 72 corresponding to CI numbers 45385, 45386 and 45370.1 respectively. A preferred polar indicator of this invention is ESTOFIL BLUE S-RLS ($C_{44}H_{52}N_4O_6S_2$, also known as Solvent Blue 45 or 3,3'-[(9, 10-dihydro-9,10-dioxo-1,4-anthracenediyl)dilimino]bis[N-cyclohexyl-2,4,6-trimethyl-sulfonamide), with a CAS registry number of 23552-74-1.

For ease of visual determination, the polar indicator should be of a color that contrasts with the color of tested oil. More vibrant colors are generally preferred, such as magentas or reds and darker shades of blue or green, and the like. The polar indicators should be heat stable (i.e., still visualizable and able to be displaced by the polar compounds in the oil when bound to the adsorbent) at least up to the temperature of the assay, such as, for example, heat stable up to at least about 180° C.

Very little polar indicator is required for use in a given test. For example, a spot of about 1 microliter ($\mu l$) of about 0.2% ESTOFIL BLUE S-RLS onto the adsorbent is typically sufficient for a test strip of about 7 cm$^2$. Those skilled in the art will recognize that the amount of polar indicator should not be so great that it creates a thickly smeared migrating polar indicator front on the solid surface resulting in an inaccurate measurement of the distance between the mobilized polar indicator front and a fixed point such as the base of the adsorbent surface or the point of polar indicator application. The amount of polar indicator should also not be so-small that the polar indicator cannot be detected once it has been mobilized from its point of application.

It is understood by those of skill in the art that there are other compounds that can be used in place of colored polar dyes. Other polar indicator compounds that can be mobilized from the adsorbent surface in the presence of polar compounds in an oil sample, include, but are not limited to: suitable fluorescent dyes that can be visualized using ultraviolet light; polar amine-containing compounds that can be visualized using silver or other amine reactive compounds to produce a visible reaction product; or a polar proteinaceous material that can be visualized by ninhydrin, for example.

The Rf values of an oil under a variety of degradative conditions can be plotted for a particular adsorbent surface and optionally for a particular device design and compared to the percentage of total polar compounds in the oil as determined using ISO 8420. The results of such a graph provide a range of Rf values that correlate with a particular percentage of polar compounds to provide a threshold for discarding oil based on a predetermined standard such as, for example, government regulations. FIG. 1 is a graph correlating the Rf values for a variety of oils using an adsorbent surface as provided in Example 1 with the percentage of polar compounds in the oil as determined by ISO 8420. The graph indicates that there is a direct correlation between the Rf value and the amount of polar compounds in the oils.

Figure 2:
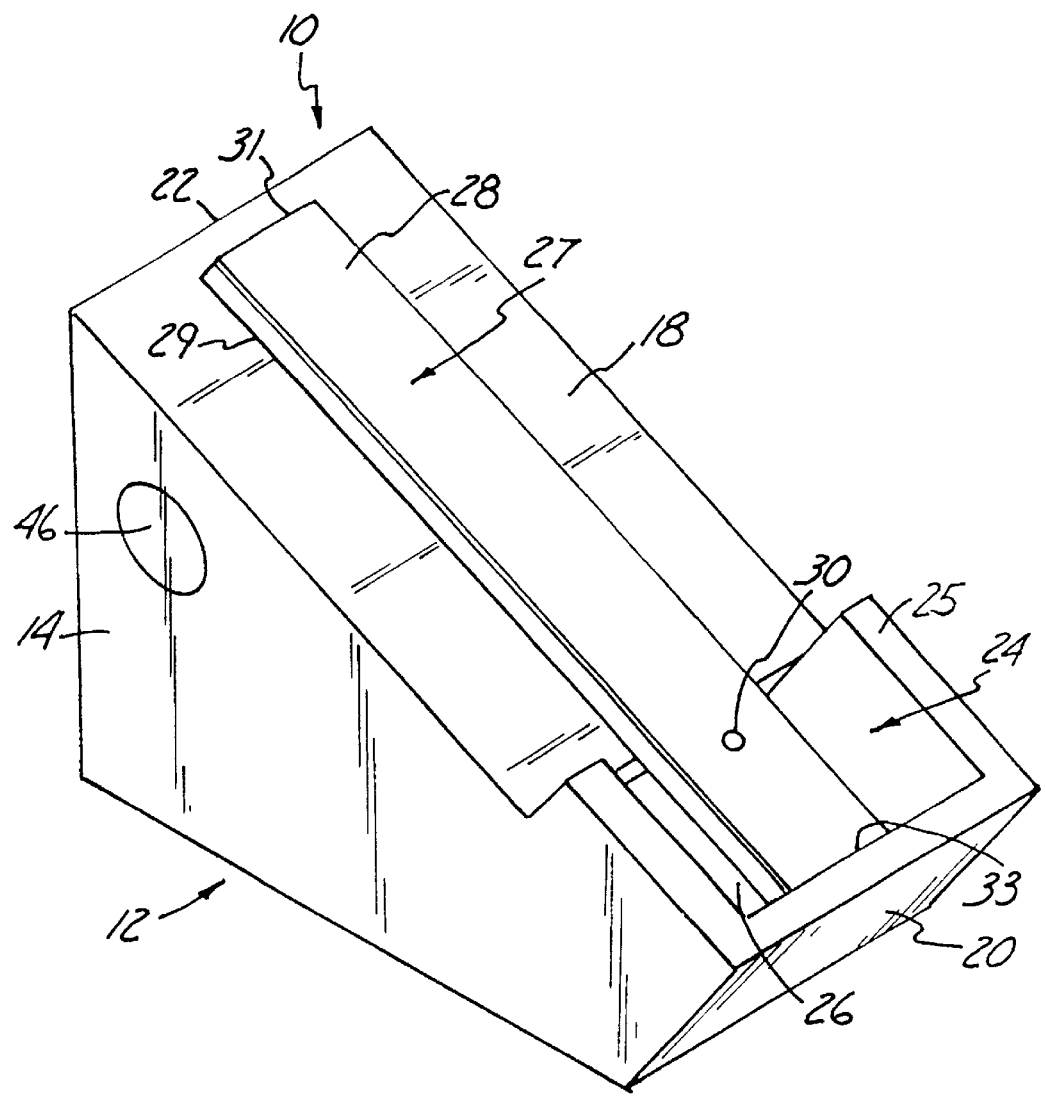
FIG. 2 is a perspective view of a first device according to this invention.

The present invention also relates to devices for determining the amount of polar compounds in oil. The device preferably provides a heat conducting support for the test surface. In a preferred device 10 illustrated in FIG. 2, the heat conducting support is a block, preferably prepared from a solid heat-conducting material, that provides support to the test surface and can preferably conduct heat to the entire length of the test surface. The device 10 of FIG. 2 includes a base 12, sides 14, top face 15 and ends 20 and 22. At least one support surface 18 extends from a sample reservoir 24 along the top face 15 of the device 10. In the embodiment of FIG. 2, top face 15 forms a support surface 18 and support surface 18 is preferably angled relative to base 12 such that the angle of the support surface 18 is preferably about 10° to about 80° from a horizontal plane containing base 12. More preferably, the angle of the support surface 18 relative to the base is about 20° to about 70° and in a particularly preferred embodiment the angle is about 30°. The angle of the support surface assists in retaining the oil sample in the sample reservoir 24, facilitates uniform migration of the oil along a test strip 27, improves the heat conductivity of the device, and eases visualization of the oil and polar indicator front as the oil migrates over the adsorbent. As a result of the angled nature of support surface 18, an end 20 closest to sample reservoir 24 is shorter in height relative to end 22. Sample reservoir 24 can take any of a variety of configurations and in the embodiment illustrated in FIG. 2, sample reservoir 24 is formed from one or more lips 25 extending from end 20 and from at least a portion of sides 14. In a preferred embodiment, support surface 18 includes a recessed face portion 26 that is parallel to and recessed relative to the plane formed from support surface 18 (see cross-section in FIG. 3).

The invention also relates to a system comprising a device, according to this invention, and a test surface. In use, a test surface, here a test strip 27 (FIG. 2), having a top edge 31 and a bottom edge 33 and comprising a solid surface or backing 29 and an adsorbent 28 coated onto solid surface 29 is positioned onto support surface 18 of device 10. In a preferred embodiment, a spot of polar indicator 30 is positioned near bottom edge 33 (preferably centered in the lower one-fourth of test strip 27). Preferably, the polar indicator is applied to the adsorbent in a small volume and allowed to dry. Polar indicator 30 can also be dispersed in the adsorbent. The polar indicator 30 is preferably applied at least to the lower aspect of test strip 27 and where the polar indicator is spotted onto the adsorbent, the polar indicator is positioned on the test strip near sample reservoir 24. Support surface 18 can be any of a variety of dimensions in width and is at least as wide as the width of the test strip 27 and preferably at least as wide as the width of the adsorbent 28. Test strip 27 can be of any length, but preferably less than or equal to the length of the top face 15. Test strip 27 can be longer than top face 15 but may not obtain the heat conducting benefit that is provided when there is direct contact between support surface 18 and test strip 27. The device 10 is preferably heated for a time on a heat source such as a hot plate, a fry griddle, or the like. Heating is not necessary when the oil is able to migrate over the adsorbent at room temperature; however, heating can reduce the viscosity of the oil to permit solids and viscous oils to be assessed for the presence of polar compounds in the oil. A sample of oil, preferably about 0.5 ml to about 10 ml, and more preferably about 1 ml, depending on the size of the sample reservoir, is added to the sample reservoir 24. The amount of oil should be sufficient to saturate the adsorbent 28. The oil can be added hot or cold into the sample reservoir 24. Preferably, but not required, the test strip 27 is positioned on the device before the oil is added. The device is incubated for a sufficient time to permit the oil front to migrate on the test strip past the polar indicator and to permit the polar indicator to mobilize on the adsorbent surface if sufficient polar compounds are present in the oil sample. Incubation can be conducted at room temperature or at an elevated temperature, as discussed above.

Figure 3:
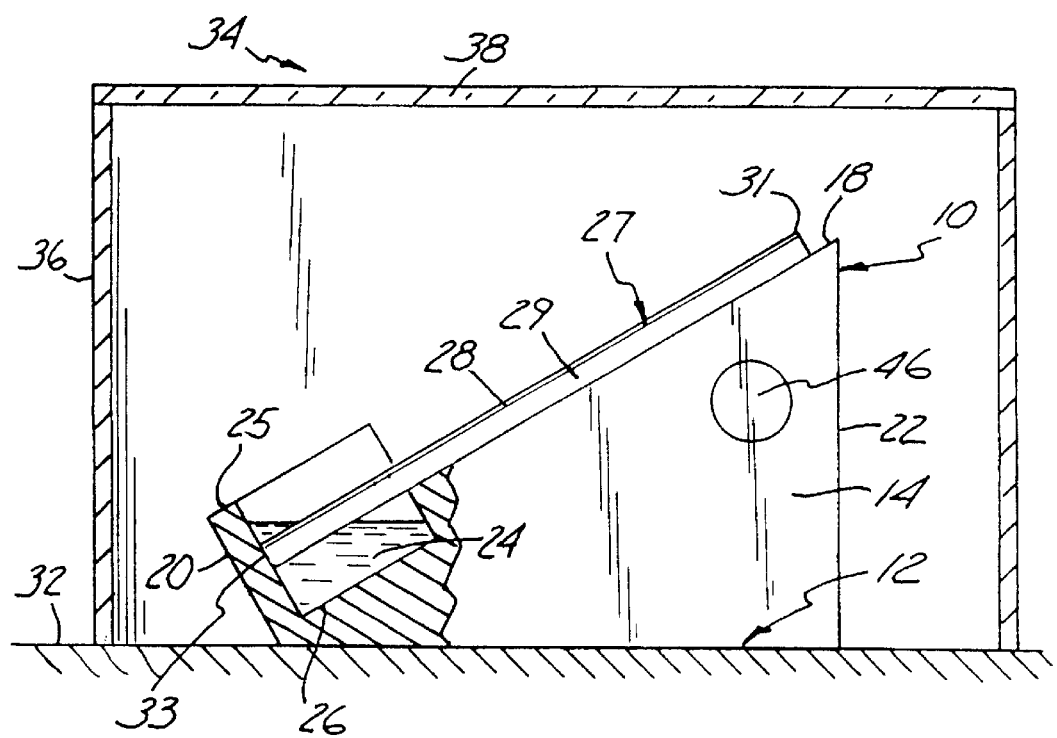
FIG. 3 is a side elevation view, partially in cross-section of the device of FIG. 2 and covered with a first covering according to this invention.
Figure 4:
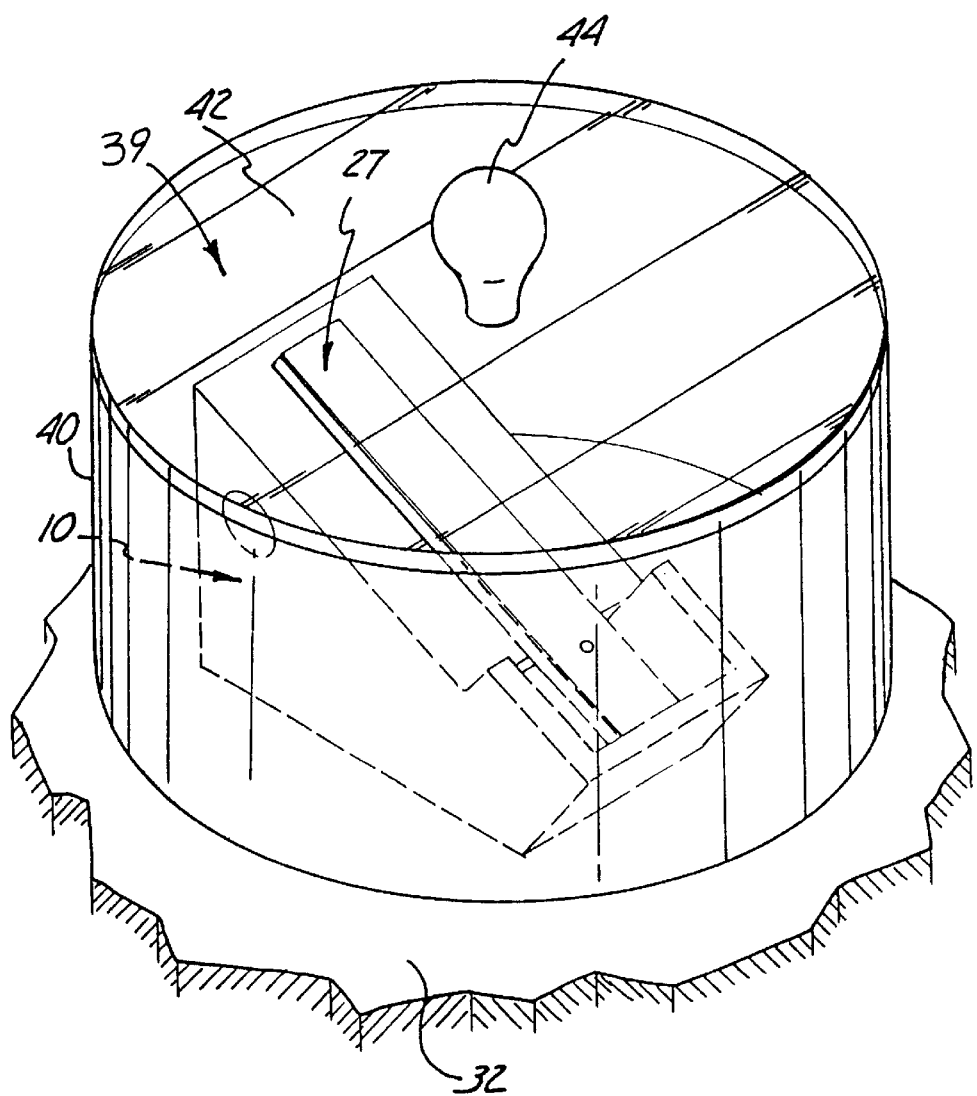
FIG. 4 is a perspective view of the device of FIG. 2 and covered with a second covering according to this invention.

The device 10 is provided in cross-section in FIG. 3 positioned on a heated surface 32. A cover 34 is positioned over the device 10 to provide uniform heat to the oil as it migrates over the adsorbent 28. The cover 34 can take any three dimensional shape and preferably provides a dome-like covering over device 10 while resting on a heated surface 32, such as a griddle, a surface of an oven, and the like. In the device illustrated in FIG. 3, the cover 34 is a substantially rectangular covering with sides 36 and top 38. In FIG. 4, a cover 39 is substantially circular in cross-section with side 40 and a circular top 42. A handle 44 is preferably included to facilitate easy manipulation of the cover on the heated surface 32. In a preferred embodiment, the sides of the covers of this invention are prepared from a break-resistant substance such as teflon, fiberglass, ceramic, and the like and the top, or at least a portion of the top of the covers of this invention are prepared from a heat-resistant substantially transparent substance, such as a heat-resistant plastic including, but not limited to, polyester, acrylic, polycarbonate, and the like.

It will be understood that the device provided in FIG. 2 can take on a variety of dimensions. As noted above, the width of support surface 18 is sufficiently wide to support at least one test strip comprising an adsorbent. It will be understood that the device can be of a variety of sizes to accommodate a variety of test strip dimensions and geometries. The adsorbent on the solid surface 29 is sufficiently long to permit the polar indicator 30 to migrate in the presence of the oil sample from the point of polar indicator application to provide two readily measured points: the distance that the polar indicator has migrated relative to a fixed point (e.g., the lower aspect of the adsorbent or backing, or the point of polar indicator application) and the distance that the oil front has migrated.

The test surface 27 comprises a solid surface or backing 29 and an adsorbent 28 is about 5 centimeters (cm) to about 15 cm in length and preferably about 7 cm to about 10 cm in length. The backing with adsorbent is preferably about 7 millimeters (mm) in width to about 15 mm in width and preferably about 10 mm in width. The device 10 has a support surface 18 that is preferably at least as long as the length of the adsorbent on the backing. The sample reservoir preferably holds at least a sample of 0.5 ml. The level of oil in the sample reservoir is below the polar indicator spot 30. In a preferred device 10, the base 12 of the device is preferably about 72 mm long and about 60 mm wide with a height at end 20 of 15 mm and a height at end 22 of about 43 mm. In a preferred device, the angle of face 18 relative to the base is preferably about 30° and generally about 20° to about 70°. In a device with these dimensions, the test is considered to be complete when the oil front has migrated over the adsorbent material on the solid surface for about 50 mm relative to the lower edge of the adsorbent material. Those of ordinary skill in the art will recognize that the dimensions of the device can be varied without undue experimentation and that the calibration (i.e., the determination of threshold Rf values for oils) of differently sized devices can also be performed without undue experimentation.

Preferably, the support surface 18 is prepared from a material that conducts heat well. Examples of such materials include, but are not limited to, aluminum, copper, stainless steel, iron, zinc, tin and other heat conducting materials. Preferably the heat conducting material is aluminum. In a preferred embodiment device 10 is prepared from a heat conducting material, such as aluminum.

In the device of FIG. 2, and using a test strip with an adsorbent prepared from silica, a 25% threshold for the percentage of total polar compounds in fats and oils, as required by some European countries, correlates to an Rf value of about 0.52 to about 0.54. Restaurants in countries mandating disposal of oils with 25% total polar compounds in the oil would preferably discard oil with an Rf value of at least about 0.52 to at least about 0.54.

The device 10 and other devices according to this invention can include a variety of sensors or markers. For example, at least one temperature sensor can be affixed to a surface of device 10 to monitor temperature during the course of the testing period. There are a variety of temperature sensors that would be suitable with this device including, but not limited to, adhesive temperature sensor devices as well as a variety of heat sensor devices such as those available from Pacific Transducer Corporation (Los Angeles, Calif.), and the like. Similarly, a well could be provided in an end of the device that is adapted to fit a thermometer, or another heat sensing device, such as an electronic device, or the like. Those skilled in the art will recognize that the temperature sensor could be positioned in a variety of locations on the devices of this invention or, alternatively, on a cover of this device.

Markers can be included in the device such as marks in the device to indicate when the test is complete as based on the migration of the oil front, for example. In another example, where the device is sold in a country regulating a threshold level of polar compounds in oil, the device can include markings providing ranges for polar indicator front mobility relative to a marking for the oil front to indicate ranges of oil that have an acceptable level of polar compounds in the oil. Markings for levels of oil in the oil reservoir can also be included. The markings can take on a variety of forms, including, but not limited to, etched marks, adhesive markings, colored markings, and the like.

In addition, the devices of this invention can also incorporate a heating source or heat element such that the support surface can be heated from an internal heat source.

While FIGS. 2–4 illustrate a single welled device, other configurations of this device are possible. In one embodiment, it is possible to modify device 10 to include interlocking members such that a plurality of devices according to device 10 can interlock to form a multi-well device for the simultaneous or sequential measurement of more than one sample. FIG. 5 illustrates a multi-welled device 47 according to this invention with a plurality of sample reservoirs. In FIG. 5, the device is substantially similar to that of FIG. 2. The device 47 has a base (not shown), sides 48, a top face 50 comprising a plurality of support surfaces 52, ends 54 and 56, a plurality of sample reservoirs 58 and a plurality of recessed faces 60. Lips 60, or equivalent means, are used to separate the sample reservoirs 58 so that samples of oil do not cross-contaminate separate test strips. In this embodiment, one or more samples of oil can be tested simultaneously or sequentially. The device of FIG. 5 includes 3 test strips 27 positioned along each support surface 52. Optionally, a temperature sensor can be included.

In use, as provided in FIG. 6, device 47 is positioned on a heated surface 66 with at least one test strip 27 in place. One or more samples of oil are placed separately in the sample reservoirs 58. A cover 68 is adapted to fit over device 47. Cover 68 is adapted with sides 70, top 72 and handle 74. Preferably at least a portion, such as top 72, of cover 68 is transparent.

The device of this invention can be prepared in a variety of configurations. For example, in another embodiment of the device of this invention, illustrated in FIG. 7, the device 76 comprises a test surface 78 and a cover 80. In this embodiment, the cover 80 can rest directly on test surface 78.

The test surface 78 comprises an adsorbent 82 on a solid surface 84, according to this invention, and a sample of polar indicator, also according to this invention, is spotted, preferably in a plurality of spots 83 or as a ring of polar indicator positioned on adsorbent 82 preferably at least about within one fourth of the distance from a sample reservoir 88 to the point of contact between the cover 80 and the test surface 78. The test surface 78 is positioned horizontally on a heated surface 86.

A sample reservoir 88 is provided in fluid communication with the test surface 78. The sample reservoir 88 can comprise a portion of a solid surface 84 without a coating of adsorbent thereon. In another embodiment, the sample reservoir 88 can comprise a depression in the solid surface 84. Other configurations for reservoir 88 will be apparent to those of ordinary skill in the art. The cover 80 is preferably a dome shaped device, although those of ordinary skill in the art will recognize that the cover 80 can take on a variety of geometries without detracting from the scope of the invention. In the embodiment of FIG. 7, the cover 80 has a substantially circular cross-section and includes side 90 and a top 92. The cover 80 optionally also includes a test sample delivery system to introduce an oil sample to be tested into sample reservoir 88. In the embodiment of FIG. 7, the test sample delivery system includes a housing to hold at least one oil sample and means to slowly feed oil into sample reservoir 88, such as a dropper apparatus 94. Where sample reservoir 88 includes a depression in solid surface 84, a dropper apparatus 94 or other sample delivery system may not be needed in cover 80, as the oil sample can be loaded directly into sample reservoir 88.

The device 76 is shown in cross-section in FIG. 8. Test surface 78 comprising adsorbent 82 on a solid surface 84 is positioned on a heated surface 86, such as a griddle, a hot plate, or in an oven. A cover 80 is centered such that dropper apparatus 94 is centered over sample reservoir 88. The dropper apparatus in the embodiment of FIG. 7 and 8 includes a support 96 to removably hold a dropper 98 in place over sample reservoir 88. In FIG. 7 and FIG. 8 the sample delivery system also includes a means for slowly adding the oil sample to sample reservoir 88. In the embodiment of FIG. 7, this means is a bulb 100.

Those of ordinary skill in the art will recognize that there are a variety of sample delivery systems and means for slowly introducing the oil sample through cover 80 into sample reservoir 88. For example, a capillary tube connected through the cover to an oil sample reservoir with a pump, such as a peristaltic pump, or the like, can be used to slowly introduce oil into the sample. These methods for introducing oil into the sample reservoir 88 are technologies known in the art and should not detract from the spirit of this invention. Like the embodiments previously described, the test surface 78 is heat resistant (i.e., not deformable), preferably up to about 170° C. In the embodiments of FIGS. 7 and 8, the oil migrates as an ever widening circle away from sample reservoir 88. The Rf value is calculated as a ratio of the distance the polar indicator has migrated from a fixed point relative to the distance that the oil front has migrated from the same fixed point. Preferably, the fixed point is the point of application of the polar indicator sample or the edge of sample reservoir 88. If necessary, a plurality of measurements can be taken based on the plurality of polar indicator spots or based on multiple measurements from a circumferential ring of polar indicator and used to create a mean Rf value.

In another configuration of a device for testing for the presence of polar compounds in oil, that is not illustrated herein, the device includes a test surface or strip comprising an adsorbent on a solid surface with a polar indicator positioned near, but at a distance from the bottom edge of the adsorbent material. The test surface is positioned in a substantially vertical position in a chamber. The chamber preferably has a base, sides and a cover. The chamber is preferably sufficiently large to entirely contain the solid surface. However, it will be understood that the solid surface can extend from the chamber just as the test strip can extend beyond the support surface of the embodiments illustrated in FIGS. 2 to 6. Preferably, the test surface rests within the chamber along the base of the chamber and is supported at least two points by the inner sides of the chamber. That is, the chamber can be of a variety of shapes including cylindrical, rectangular, and the like. Also, preferably, the angle of the solid surface relative to the base of the chamber is preferably greater than 45°. A test sample of oil is placed in the bottom of the chamber in an amount sufficient to contact and saturate the adsorbent surface but rising to an initial level below the level of the polar indicator spot. The chamber is preferably sealed and preferably placed in a heated environment, such as an oven, a hot plate, griddle or other heat source for a time sufficient for the migrating oil front to mobilize the polar indicator and for the oil front to migrate a measurable distance beyond the polar indicator front. In effect, the sample of oil in this invention is the solvent for the polar indicator. Again, the Rf value is calculated as described above.

Another aspect of this invention relates to a kit to be supplied to individuals, companies, service providers and the like who are in need of assessing the quality of an oil containing polar compounds. The kit preferably includes a device in accordance with this invention, at least one test strip or test surface comprising an adsorbent precoated on a solid surface and including a polar indicator prespotted onto the adsorbent of each test strip or test surface. The kit can optionally include a cover, in accordance with this invention, a sample of pure oil to use as a control, a sample of polar indicator to be added to the test strip or test surface, a sampling device to facilitate removing a sample of oil and applying it to an oil reservoir of the devices of this invention, and written guidelines and instructions for the device and for ranges of Rf values correlating to percent ranges of polar compounds in an oil sample measured by a particular device. A heat source with a surface capable of being heated can also be supplied if necessary; however, in a preferred mode of operation, the devices of this invention are adapted to fit into most restaurant kitchens and can be used on griddles and/or in ovens or alternatively incorporate a heat source directly into the device.

The devices of this invention are reusable and readily cleanable. For example, the device can be allowed to cool and wiped clean. Advantageously, the assay works without filtration or other oil sample preparation steps.

All references and publications cited herein are expressly incorporated by reference into this disclosure.

EXAMPLE 1

Test for Determining the Presence of Polar Compounds in Oils and Correlation of the Test to ISO 8420

Samples were tested using the methods of this invention and compared to the results as determined using ISO 8420.

Oil Samples: A sample of fresh oil (i.e., unused oil), oil identified as used but still acceptable for frying, and oil identified as used and no longer acceptable for frying (oil which had been or was to be discarded) was obtained from local fast food restaurants as indicated in Table 1. The unused oil is identified hereinafter as "fresh," the used but still acceptable oil as "in use," and the no longer acceptable oil as "discarded."

Samples of frying oils collected from fast food chains (test site A-D) in the US and outside the United States (OUS) were used in the study. These oils were used for frying fish, chicken, french fries, pie, onion rings and other types of food. The samples were collected from fresh oil and from oil that had been used for various times and therefore represent oils with varying levels of degradation.

Plate Preparation: A glass-backed silica gel thin layer chromatography plate, commercially available from the Whatman Company (Clifton, N.J.) as a Diamond Series K6F plate (with a 250 micron thick coating with 60 angstrom pore size and between 10–12 micron particle size), was cut into small strips 10 mm wide by 67 mm long.

A 0.2% dye solution was prepared by dissolving 200 mg ESTOFIL S-RLS dye powder, obtained from Clariant Corp (Charlotte, N.C.) in 100 g toluene. One microliter of dye solution was spotted onto the silica gel strip such that the spot was centered in the width of the strip and approximately 5 mm from one end (that designated as the base of the strip, i.e., the portion of the strip contacting the sample reservoir). The spot was allowed to dry at ambient conditions.

A device was prepared in accordance with the description of FIGS. 2–4. The device was prepared from aluminum and was 43 mm high, 72 mm long and 60 mm wide with an angled support surface relative to the base of the device of about 30°.

The aluminum block was preheated by placing it on a laboratory hot plate set at about 170° C for approximately 30 minutes. The polar indicator-spotted strip was placed onto the block with the base of the strip adjacent the oil reservoir of the block and with the polar indicator spot facing away from the reservoir. After 2 minutes, 1 ml of testing oil was added, preferably, drop-wise into the reservoir, making sure that oil did not touch the polar indicator directly. After the oil was added, the block was covered. Once the oil front reached a distance of about 50 mm from the base of the test strip (generally between about 25 to about 35 minutes), the test strip was removed. The distance traveled by the polar indicator was measured from base of the test strip and the distance traveled by the oil front from the base of the test strip was also measured. This ratio of distance polar indicator traveled/distance traveled by the oil front was termed Rf and represents the level of polar compounds in the oil.

In a specific example, sample 5, oil obtained from a local fast food restaurant (site B) was added to the reservoir dropwise until the oil level was just below the polar indicator spot on the strip. Approximately one milliliter of oil was used. The oil level did not touch or cover the polar indicator spot. This prevents the polar indicator from dissolving in the oil. A transparent heat resistant cover was placed over the block and the oil was allowed to migrate up the strip until the oil front reached a mark on the block designating a travel distance of about 50 mm from the base of the strip (generally an incubation time of about 25 to about 35 minutes). The strip was then removed from the block. Using a ruler, the distance from the base traveled by the polar indicator front was determined to be about 22 mm. The distance from the base traveled by the oil front was determined to be about 50 mm. The Rf or ratio of fronts was calculated by dividing the distance traveled by the polar indicator front by the distance traveled by the oil front. In this example, the Rf calculated to 0.44.

$$Rf = \frac{d_1}{d_2}$$

where $d_1$ is the distance that the polar indicator front migrates relative to a fixed point $d_0$ and $d_2$ is the distance that the oil front migrates relative to the same fixed point $d_0$. Preferably the fixed point, $d_0$, is the base of the test strip or the point of polar indicator application.

ISO 8420, determination of percentage of polar compounds: To determine the total percentage of polar compounds in the oil, a method, ISO 8420:1990(E), "Determination of Polar Compounds Content in Animal and Vegetable Fats and Oils" was used. This method employs column chromatography and is an industry standard method for separating polar compounds from degraded or used frying oils to quantitate the polar compounds in the oils.

Briefly, in this method a glass rod containing a wad of cotton wool was placed in the lower part of the column. Air was removed by pressing the cotton wool down with the rod. About 30 ml of elution solvent (mix of 87 volumes of chromatographic quality light petroleum (boiling range 40° C. to 60° C.) and 13 volumes of stabilized diethyl ether) was added to the column.

A slurry of silica gel was prepared in a 100 ml beaker using about 80 ml of the elution solvent. The slurry was poured into the column using a funnel. The transfer of the silica gel into the column was completed by rinsing the beaker with the elution solvent. The stopcock on the chromatography device was opened and the elution solvent was run off until the level of the elution solvent was about 100 mm above the silica gel. The silica gel was leveled by tapping the column and a sand layer was positioned on top of the silica gel. The supernatant elution solvent was run off to within 10 mm of the sand layer.

The test sample was weighed to the nearest 1 mg and 2.5 g+/-0.1 g of the test sample was added to a 50 ml volumetric flask. The test portion was dissolved in about 20 ml of the elution solvent by slight warming. The elution solvent was allowed to cool to room temperature and was diluted to 50 ml with elution solvent.

A 250 ml flask was dried and the flask was weighed and placed beneath the column to collect sample. Twenty milliliters of the test solution was transferred to the prepared column. The stopcock was opened and the solvent allowed to run off down to the level of the top of the sand layer. The eluate (containing nonpolar compounds) was collected in the 250 ml flask. The nonpolar compounds were allowed to elute by adding 150 ml of the elution solvent via a dropping funnel. The flow-rate was adjusted so that the 150 ml volume could pass through the column in about 60 min to about 70 min. After completion of the elution, material adhering to the outlet of the column was washed using elution solvent. The solvent was removed from the flask under vacuum, typically with the aid of a rotary evaporator and a water-bath controlled at a temperature no higher than 60° C. Nitrogen was added into the system to complete the evaporation process. The flask was weighed to the nearest 1 mg.

The content of polar compounds was determined as a percentage by mass given by the formula:

$$\frac{m_1 - (5/2)m_2 - m_3}{m_1} \times 100$$

where $m_1$ is the mass, in grams, of the test portion, $m_2$ is the mass, in grams of the non-polar fraction; and m3 is the mass, in grams of the elution blank.

Analysis of the results showed a good correlation between the Rf values obtained using the methods of this invention as compared with the % polar compounds determined by the column chromatographic method (see FIG. 1). The higher the Rf value, the higher the % polar compounds produced in the frying oils. The results indicated that one could predetermine the Rf value knowing the percentage of polar compounds in the oil and similarly, knowing the % of polar compounds in the oil permitted the determination of the Rf value of the sample.

TABLE 1

Comparison of Rf value to % Polar Compounds determined using ISO8420

| Sample | Source | Rf | % Polar Compounds |
|---|---|---|---|
| 1 | Oil A: fresh oil (US) | 0.22 | 2.85 |
| 2 | Oil B: fresh oil (US) | 0.22 | 2.17 |
| 3 | Oil C: fresh oil (OUS) | 0.24 | 6.18 |
| 4 | Oil A: used oil (in use) | 0.30 | 10.12 |
| 5 | Oil B: used oil (in use) | 0.44 | 19.13 |
| 6 | Oil C: used (chicken fried, in use) | 0.54 | 25.60 |
| 7 | Oil C: used (fish fried, in use) | 0.42 | 18.27 |
| 8 | Oil C: used (french fries, in use) | 0.41 | 15.70 |
| 9 | Oil A: used (discarded) | 0.53 | 23.19 |
| 10 | Oil B: used (discarded) | 0.70 | 36.80 |
| 11 | Oil C: used (discarded) | 0.51 | 25.28 |
| 12 | Oil D: used (chicken fried, discarded) | 0.45 | 17.85 |

FIG. 1 is a graph plotting the Rf data of Table 1 with the % of polar compounds as determined using ISO 8420: "Determination of Polar Compounds Content in Animal and Vegetable Fats and Oils."

The correlation graph (FIG. 1) demonstrates the results of this study. At a level of 25% polar compounds, the corresponding Rf is 0.53. Therefore, on the block, the distance the polar indicator travels relative to the 50 mm (fixed) oil front is 26.5 mm. A variety of oils, according to this invention, that displace the polar indicator beyond the 26.5 mm mark in the device according to this example, should be discarded. Where the polar indicator height is less than 26.5 mm, using a 25% polar compound cut-off, this oil is still useable.

It will be appreciated by those skilled in the art that while the invention has been described above in connection with particular embodiments and, examples, the invention is not necessarily so limited and that numerous other embodiments, examples, uses, modifications and departures from the embodiments, examples and uses may be made without departing from the inventive scope of this application.

What is claimed is:

1. A system for determining polar compounds in oil comprising:
   a heat conducting device comprising a base, at least one sample reservoir adapted to contain a sample of oil comprising polar compounds, and at least one support surface adapted to support at least one test surface; wherein the support surface is angled relative to a plane containing the base of the device and wherein the sample reservoir is in fluid communication with the test surface when oil is in the sample reservoir; and
   at least one test surface comprising an adsorbent positioned on a backing wherein the adsorbent comprises a polar indicator.

2. The system of claim 1 further comprising a cover adapted to cover the heat conducting device.

3. The system of claim 2 wherein the cover comprises a transparent portion.

4. The system of claim 2 wherein the cover comprises a handle.

5. The system of claim 1 wherein the device comprises a plurality of sample reservoirs.

6. The system of claim 1 wherein the angle of the support surface relative to the base of the device is about 10° to about 80°.

7. The system of claim 1 wherein the angle of the support surface relative to the base of the device is about 20° to about 70°.

8. The system of claim 1 wherein the device comprises a solid block of a heat-conducting material.

9. The system of claim 1 wherein the device further comprises a temperature indicator.

10. The system of claim 1 wherein the heat conducting device is prepared from a material selected from the group consisting of aluminum, copper, stainless, steel, iron, zinc and tin.

11. The system of claim 1 wherein the adsorbent is selected from the group consisting of silica, aluminum oxide, and cellulose.

12. The system of claim 1 wherein the backing is selected from the group consisting of glass, paper, aluminum and heat-resistant plastic.

13. The system of claim 1 wherein the oil is selected from the group consisting of lard, corn oil, peanut oil, canola oil, olive oil, palm oil, palm kernel oil, coconut-oil, red palm oil, and combinations thereof.

14. The system of claim 1 wherein the device further comprises a heat source housed in the device.

15. The system of claim 1 wherein the polar indicator is a polar colored dye.

16. The system of claim 1 wherein the polar indicator is a dye that has less affinity for the adsorbent than the polar compounds in the oil and more affinity for the absorbent than unused oil.

17. The system of claim 1 wherein the dye comprises $C_{44}H_{52}N_4O_6S_2$.

18. A device for determining polar compounds in oil comprising:
   a base;
   at least one test surface comprising an adsorbent, with a polar indicator positioned thereon, and a backing wherein the test surface is angled relative to the plane containing the base; and
   at least one sample reservoir positioned adjacent to the test surface to establish fluid communication therewith when oil is present in the sample reservoir.

19. The device of claim 18 additionally comprising a cover.

20. The device of claim 18 wherein the angle of the test surface relative to the base is about 10° to about 80°.

* * * * *

UNITED STATES PATENT AND TRADEMARK OFFICE
CERTIFICATE OF CORRECTION

PATENT NO.   : 6,436,713 B1
DATED        : August 20, 2002
INVENTOR(S)  : Onwumere, Fidelis C.

It is certified that error appears in the above-identified patent and that said Letters Patent is hereby corrected as shown below:

<u>Title page,</u>
Item [57], ABSTRACT,
Line 1, "methods" should read -- systems --;

<u>Column 2,</u>
Line 36, "2%1" should read -- 21% --

<u>Column 3,</u>
Line 24, "herein after" should read -- hereinafter --
Line 30, "are. complex" should read -- are complex --

<u>Column 4,</u>
Line 8, "thereof In" should read -- thereof. In --
Line 26, "comprising" should read -- comprise --
Lines 55 and 67, "comprises" should read -- comprise --

<u>Column 5,</u>
Line 11, "thereof In" should read -- thereof. In --

<u>Column 7,</u>
Line 18, "here" should read -- herein --
Line 38, "restaurants-may" should read -- restaurants may --
Line 49, "canola, olive, palm," should read -- canola oil, olive oil, palm oil, --
Line 50, "coconut," should read -- coconut oil, --
Line 66, "1 80ºC.," should read -- 180ºC., --

<u>Column 9,</u>
Line 34, "so-small" should read -- so small --

<u>Column 10,</u>
Line 28, "here" should read -- herein --

<u>Column 13,</u>
Line 39, "FIG. 7 and 8" should read -- FIGS. 7 and 8 --

UNITED STATES PATENT AND TRADEMARK OFFICE
CERTIFICATE OF CORRECTION

PATENT NO. : 6,436,713 B1
DATED : August 20, 2002
INVENTOR(S) : Onwumere, Fidelis C.

It is certified that error appears in the above-identified patent and that said Letters Patent is hereby corrected as shown below:

Column 18,
Line 37, "coconut-oil" should read -- coconut oil --
Line 45, "absorbent" should read -- adsorbent --

Signed and Sealed this

Sixth Day of May, 2003

JAMES E. ROGAN
*Director of the United States Patent and Trademark Office*